(12) United States Patent
Buell

(10) Patent No.: US 10,278,987 B2
(45) Date of Patent: *May 7, 2019

(54) METHODS OF TREATING OPTIC DISORDERS

(71) Applicant: Brian W. Buell, Fayetteville, AR (US)

(72) Inventor: Brian W. Buell, Fayetteville, AR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/714,802

(22) Filed: Sep. 25, 2017

(65) Prior Publication Data

US 2018/0028556 A1 Feb. 1, 2018

Related U.S. Application Data

(60) Division of application No. 14/459,771, filed on Aug. 14, 2014, now Pat. No. 9,770,464, which is a continuation of application No. 13/166,207, filed on Jun. 22, 2011, now Pat. No. 8,822,431.

(60) Provisional application No. 61/358,522, filed on Jun. 25, 2010.

(51) Int. Cl.
| | | |
|---|---|---|
| A61K 31/714 | (2006.01) | |
| A61K 31/4415 | (2006.01) | |
| A61K 31/519 | (2006.01) | |
| A61K 31/593 | (2006.01) | |

(52) U.S. Cl.
CPC ........ *A61K 31/714* (2013.01); *A61K 31/4415* (2013.01); *A61K 31/519* (2013.01); *A61K 31/593* (2013.01)

(58) Field of Classification Search
None
See application file for complete search history.

(56) References Cited

U.S. PATENT DOCUMENTS

| | | | |
|---|---|---|---|
| 6,103,756 A | 8/2000 | Gorsek | |
| 8,822,431 B2 * | 9/2014 | Buell | A61K 31/4415 514/52 |
| 9,770,464 B2 | 9/2017 | Buell | |
| 2003/0220225 A1 | 11/2003 | Sosnowski et al. | |
| 2004/0116351 A1 | 6/2004 | Halevie-Goldman | |
| 2006/0281822 A1 | 12/2006 | Appleton | |

FOREIGN PATENT DOCUMENTS

| | | |
|---|---|---|
| DE | 19910682 A1 | 9/2000 |
| WO | WO-2006/099237 A1 | 9/2006 |
| WO | WO-2011/042701 A1 | 4/2011 |
| WO | WO-2011/163301 A1 | 12/2011 |

OTHER PUBLICATIONS

Salomon et al. (Ophthalmology. Apr. 1999;106(4):739-42) (Year: 1999).*
Weichel et al. (Ophthalmology vol. 115, Issue 12, Dec. 2008, pp. 2235-2245) (Year: 2008).*
B vitamins may be "silver bullet" for age-related macular degeneration: daily supplementation with folic acid plus vitamins B6 and B12 may reduce risk of AMD by 35-40 percent, (Nutrition & Fitness), Duke Medicine Health News—May 1, 2009, retrieved on Apr. 1, 2014.
"Keratoconjunctivitis Sicca", Merck Manual, http://www.merckmanuals.com/home/eye_disorders/corneal_disorders/ keratoconjunctivitis, Retrieved on Jan. 29, 2014.
Afzal, et al., "Retinal and choroidal microangiopathies: Therapeutic opportunities," Microvascular Research, vol. 74, (2007), pp. 131-144.
Aisen et al., "High-Dose B Vitamin Supplementation and Cognitive Decline in Alzheimer Disease: A Randomized Controlled TrialFREE", JAMA, vol. 300, No. 15, (2008), pp. 1774-1783.
Amilburu, et al., "Inhibition of intestinal absorption of 5-methyltetrahydrofolate by fluoxetine," J. Physiol. Biochem., 57, No. 2, (2001), pp. 71-79.
Aydemir, et al., "Plasma and Vitreous Homocysteine Concentrations in Patients with Proliferative Diabetic Retinopathy," Retina, The Journal of Retinal and Vitreous Diseases, vol. 28, No. 5, (2008), pp. 741-743.
Aydin, et al., "Association of plasma homocysteine and macular edema in type 2 diabetes mellitus," European Journal of Ophthalmology, vol. 18, No. 2, (2008), pp. 226-232.
Bartels et al., "Fibromyalgia, diagnosis and prevalence. Are gender differences explainable?", Ugeskr Laeger, vol. 171, No. 49, (2009), pp. 3588-3592. (Abstract Only).
Becker et al., "Epidemiology of homocysteine as a risk factor in diabetes", Metab. Syndr. Relat. Disord., vol. 1, No. 2, (2003), pp. 105-120.
Botto et al., "5, 10-Mehylenetetrahydrofolate Reductase Gene Variants and Congenital Anomalies: A HuGE Review", American Journal of Epidemiology, vol. 151, No. 9, pp. 862-877.
Brazionis, et al., "Homocysteine and Diabetic Retinopathy," Diabetes Care, vol. 31, No. 1, (2008), pp. 50-56.

(Continued)

*Primary Examiner* — Jeffrey S Lundgren
*Assistant Examiner* — William Y Lee
(74) *Attorney, Agent, or Firm* — Marshall, Gerstein & Borun LLP

(57) ABSTRACT

The present invention relates to methods for treating optic disorders or for reducing or alleviating the signs, symptoms, or pathological conditions related to such optic disorders. In particular, methods are provided for treating optic disorders, or reducing the symptoms thereof, the methods involving the administration of one or more downstream folate compounds and/or methyl-B12. In one particular embodiment, the method comprises administration of L-methylfolate. In other embodiments, the method involves administering both L-methylfolate and methyl-B12. In still further embodiments, the method further involves reducing dietary intake of folic acid. In certain embodiments, the method further involves identifying a subject organism with a malfunction in one or more of the folate or B4 cycles. In certain embodiments, such a malfunction is one or more of the C677T and A1298C mutations. In still further embodiments, the method further involves identifying a subject organism that is deficient in vitamins B-12 and D3 but which possesses excess homocysteine.

21 Claims, 1 Drawing Sheet

(56) References Cited

OTHER PUBLICATIONS

Cho et al., "The methylenetetrahydrofolate reductase C677T gene mutation is associated with hyperhomocysteinemia, cardiovascular disease and plasma B-type natriuretic peptide levels in Korea", Clinical Chemical Laboratory Medicine, vol. 44, Issue 9, (2006), pp. 1070-1075.
De Silva et al., "Folic acid deficiency optic neuropathy: A case report", Journal of Medical Case Reports, vol. 2, (2008), pp. 1-3.
Di Sabatino, et al., "Coeliac Disease," The Lancet, (2009), vol. 373, Issue 9673, pp. 1480-1491.
Egan, "Folic Acid Deficiency: The Benefits of L-Methylfolate Supplements", retrieved from www.pamelaegan.com on Apr. 4, 2014.
El-Asrar, et al., "Hyperhomocysteinemia and retinal vascular occlusive disease," European Journal of Ophthalmology, vol. 12, No. 6, (2002), pp. 495-500.
Fava, et al., "Folate, Vitamin B12, and Homocysteine in Major Depressive Disorder," Am. K. Psychiatry, vol. 154, No. (1997), pp. 426-428.
Ganapathy, et al., "Endogenous Elevation of Homocysteine Induces Retinal Neuron Death in the Cystathionine-6-Mutant Mouse," IOVS, vol. 50, No. 9, (2009), pp. 4460-4470.
Ghorbanihaghjo et al., "Lipoprotein(a), homocysteine, and retinal arteriosclerosis", Molecular Vision, vol. 14, pp. 1692-1697 (2008).
Giambene, et al., "Evaluation of traditional and emerging cardiovascular risk factors in patients with non-arteritic anterior ischemic optic neuropathy: a case-control study," Graefes Arch. Clin. Exp. Ophthalmol., vol. 247, (2009), pp. 693-697.
Haviv et al., "The Common Mutations C6yyT and A1298C in the Human Methylenetetrahydrofolate Reductase Gene Are Associated with Hyperhomocysteinemia and Cardiovascular Disease in Hemodialysis Patients", Nephron, vol. 92, (2002), pp. 120-126.
Haworth et al., "Symptomatic and asymptomatic methylenetetrahydrofolate reductase deficiency in two adult brothers", American Journal of Medical Genetics, vol. 45, Issue 5, (1993), pp. 572-576.
Heur, et al., "Branch retinal artery occlusion associated with compound heterozygous genotype for reductase," Doc Ophthalmol., vol. 114, (2007), pp. 163-168.
Hosoya et al., "Involvement of Reduced Folate Carrier 1 in the inner Blood-Retinal Barrier Transport of Methyltetrahydrofolate", Drug Metab. Pharmacokinet, vol. 23. No. 4, (2008), pp. 285-292.
Jiazhong, "The relationship between MTHFR gene polymorphisms, plasma homocysteine levels and diabetic in type 2 diabetes mellitus," Chinese Medical Journal, vol. 116, No. 1, (2003), pp. 145-147.
Kahleova et al., "Essential Hypertension in Adolescents: Association With Insulin Resistance and With Metabolism Homocysteine and Vitamins", American Journal of Hypertension, Ltd., vol. 15, (2002), pp. 587-864.
Kelly, et al., "Unmetabolized folic acid in serum: acute studies in subjects consuming fortified food and supplements," J. Clin Nutr, vol. 65, (1997), pp. 1790-1795.
Kim et al., "Gene-environment interactions between methylenetetrahydrofolate reductase (MTHFR) 677C>T and metabolic syndrome for the prevalence of ischemic stroke in Koreans", Neuroscience Letters, vol. 533, (2013), pp. 11-16.
Klerk et al., MTHFR 677C-->T Polymorphism and Risk of Coronary Heart Disease: A Meta-analysis, JAMA, (vol. 288, No. 16, (2002), pp. 2023-2031.
Mandecka et al., "Influence of Flickering Light on the Retinal Vessels in Diabetic Patients", Diabetes Care, vol. 30 12, (2007), pp. 3048-3052.
McEneny et al., "Folate: In vitro and in vivo effects on VLDL and LDL oxidation", International Journal for Vitamin and Nutrition Research (Impact Factor 1.27), vol. 77, No. 1, (2007) pp. 66-72.
Meletis, "Vitamin D3", retrieved from http://www.vrp.com/bone-and-joint on Jan. 29, 2014.

Micheal et al., "MTHFR gene C677T and A1298C polymorphisms and homocysteine levels in primary open angle and primary closed angle glaucoma", Molecular Vision, vol. 15, (2009), pp. 2268-2278.
Moore et al., "Apoptotic Cell Death in the Mouse Retinal Ganglion Cell Layer is Induced in vivo by the Excitatory Amino Acid Homocysteine", Experimental Eye Research, vol. 73, (2001), pp. 45-57.
Nikolaidis et al., "The Effect of Muscle-Damaging Exercise on Blood and Skeletal Muscle Oxidative Stress: magnitude and time-course considerations", Sports Med., vol. 38, No. 7, (2008), pp. 579-606.
Palomino-Morales et al., "A1298C polymorphism in the MTHFR gene predisposes to cardiovascular risk in arthritis", Arthritis Research & Therapy, 12:R71 (2010), pp. 1-8.
Pianka, et al., "Hyperhomocystinemia in Patients with Nonarteritic Anterior Ischemic Optic Neuropathy, Central Retinal Artery Occlusion, and Central Retinal Vein Occlusion," Ophthalmology, vol. 107, No. 8, (2000), pp. 1588-1592.
Polak et al., "Altered Nitric Oxide System in Patients With Open-Angle Glaucoma", Archives of Ophthalmology, American Medical Association, vol. 125, (2007), pp. 494-498.
Prinz-Langenohl, et al., "[6S]-5-methyltetrahydrofolate increases plasma folate more effectively than folic acid in women with the homozygous or wild-type 677C—T polymorphism of methylenetetrahydrofolate reductase," British Journal of Pharmacology, vol. 158, (2009), pp. 2014-2021.
Pullin et al., "Optimization of Dietary Folate or Low-Dose Folic Acid Supplements Lower Homocysteine But Do Not Enhance Endothelial Function in Healthy Adults, Irrespective of the Methylenetetrahydrofolate Reductase (C677T) Genotype", Journal of the American College of Cardiology, vol. 38, No. 7, (2001), pp. 1799-1805.
Quattrini et al., "Surrogate Markers of Small Fiber Damage in Human Diabetic Neuropathy", American Diabetes Association, vol. 56, (2007), pp. 2148-2154.
Real et al., "Association of C677T Polymorphism in MTHRF Gene, High Homocysteine and Low HDL Cholesterol Plasma Values in Heterozygous Familial Hypercholesterolemia", J. Atheroscler. Thromb., vol. 16, No. 6, (2009) 815-820.
Reynolds, "Benefits and risks of folic acid to the nervous system", J. Neurol. Neurosurg. Psychiatry, vol. 72, (2002), pp. 567-571.
Rochtchina, et al., "Elevated Serum Homocysteine, Low Serum Vitamin B12, Folate, and Age-related Macular Degeneration: The Blue Mountains Eye Study," American Journal of Ophthalmology, vol. 143, No. 2, pp. 344-346.
Roedl et al., "Increased Homocysteine Levels in Tear Fluid of Patients with Primary Open-Angle Glaucoma", Ophthalmic Research, vol. 40, (2008), pp. 249-256.
Rosenberg et al., "The Frequent 5,10-Methylenetetrahydrofolate Reductase C677T Polymorphism Is Associated with a Common Haplotype in Whites, Japanese, and Africans", American Journal of Human Genetics, vol. 70, No. 3 (2002), pp. 758-762.
Salomon et al., "Analysis of Prothrombotic and Vascular Risk Factors in Patients with Nonarteritic Anterior Ischemic Optic Neuropathy," Ophthalmology, (1999), vol. 106, No. 4, pp. 739-742.
Smith et al., "Pteridines and mono-amines: relevance to neurological damage", Postgraduate Medical Journal, vol. 62, (1986), pp. 113-123.
Sobczynska-Malefora, et al., "Erythrocyte folate and 5-methyltetrahydrofolate levels decline during 6 months of oral anticoagulation with warfarin," Blood Coagulation and Fibrinolysis, vol. 20, No. 4, (2009), pp. 297-302.
Sodi, et al., "Atherosclerotic and thrombophilic risk factors in patients with recurrent central retinal vein occlusion," European Journal of Ophthalmology, vol. 18, No. 2, (2008), pp. 233-238.
Sofi, et al., "Low vitamin B6 and folic acid levels are associated with retinal vein occlusion independently of homocystein levels," Atherosclerosis, vol. 198, (2008), pp. 223-227.
Sottilotta, et al., "Role of Hyperhomocystinemia in Retinal Vascular Occlusive Disease," Clinical and Applied Thrombosis/Hemostatis, vol. 13, No. 1, (2007), pp. 104-107.
Stahl, S., "Enhancing Outcomes from Major Depression: Using Antidepressant Combination Therapies with Multifunctional

(56) References Cited

OTHER PUBLICATIONS

Pharmacologic Mechanisms from the Initiation of Treatment," CNS Spectrums, (2010), vol. 15, Issue 2, pp. 79-94.
Stahl, S.M., "L-Methylfolate: A Vitamin for Your Monoamines," J. Clin. Psychiatry, vol. 69, No. 9, (2008), pp. 1352-1353.
Stefan et al., "The future started: nitric oxide in glaucome", Oftalmologia, vol. 51, No. 4, (2007), pp. 89-94. (Abstract Only).
Su et al., "Endothelial Dysfunction in Impaired Fasting Glycemia, Impaired Glucose Tolerance, and Type 2 Diabetes Mellitus", The American Journal of Cardiology, vol. 102, (2008), pp. 497-498.
Surtees, et al., "Association of cerebrospinal fluid deficiency of 5-methyltetrahydrofolate, but not Sadenosylmethionine, with reduced concentrations of the acid metabolites of 5-hydroxytryptamine and dopamine," Clinical Science, vol. 86, (1994), pp. 697-702.
Targher et al., "Diabetic retinopathy is associated with an increased incidence of cardiovascular events in Type 2 diabetic patients", Diabetic Medicine, vol. 25, Issue 1, (2008), pp. 45-50.
Troen, et al., "Unmetabolized Folic Acid in Plasma Is Associated with Reduced Natural Killer Cell Cytotoxicity among Women," The Journal of Nutrition, vol. 136, (2006), pp. 189-194.
Van Den Berg et al., "Hyperhomocysteinaemia and endothelial dysfunction in young patients with peripheral arterial disease", European Journal of Clinical Investigation, vol. 25, (1995), pp. 176-181.
Villa et al., "L-Folic Acid Supplementation in Healthy Postmenopausal Women: Effect on Homocysteine and Glycolipid Metabolism", The Journal of Endocrinology & Metabolism, vol. 90, No. 8, (2005), pp. 4622-4629.
Weichel et al., "Combat Ocular Tauma Visual Outcomes during Operations Iraqi and Enduring Freedom," Ophthalmology, (2008), vol. 115, No. 12, pp. 2235-2245.
Whyte et al., "The effects of acute and chronic exercise on the vasculature", Acta Physiologica, vol. 199, Issue 4, (2010), pp. 441-450.
Willems, et al., "Pharmacokinetic study on the utilisation of 5-methyltetrahydrofolate and folic acid in patients with artery disease," British Journal of Pharmacology, vol. 141, (2004), pp. 825-830.
Wollack et al., "Characterization of folate uptake by choroid plexus epithelial cells in a rat primary culture model", Journal of Neurochemistry, vol. 104, (2008), pp. 1494-1503.
Wright et al., "Homocysteine, folates, and the eye", Eye, Nature Publishing Group, vol. 22, (2008), pp. 989-993.
Wu, et al., "Blood-Brain Barrier Transport of Reduced Folic Acid," Pharmaceutical Research, vol. 16, No. 3, (1999), pp. 415-419.
Yang et al., "The impact of plasma homocysteine level on development of retinopathy in type 2 diabetes mellitus", Zhonghua Nei Ke Za Zhi, vol. 41, No. 1, (2002), pp. 34-38. (Abstract Only).
Yunus, "Role of central sensitization in symptoms beyond muscle pain, and the evaluation of a patient with widespread pain," Best Pract. Res. Clin. Rheumatol., vol. 21, No. 3, (2007), pp. 481-497. (Abstract Only).

\* cited by examiner

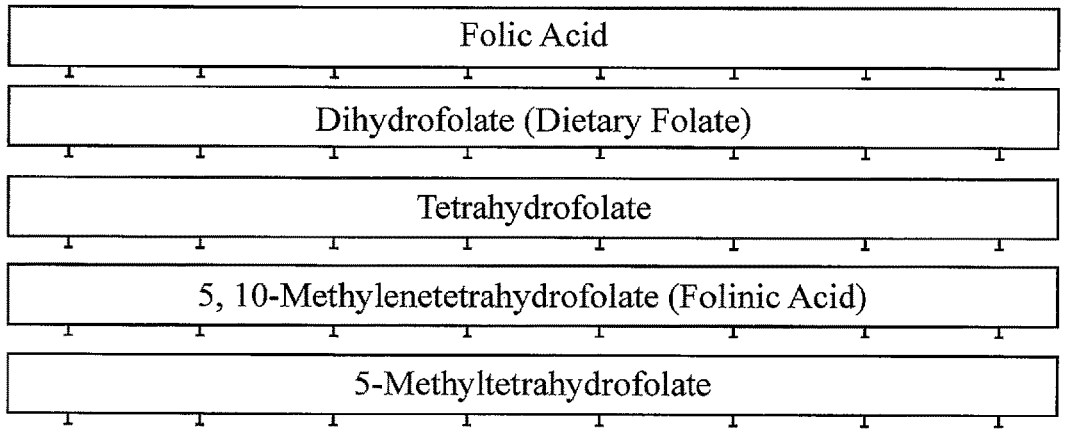
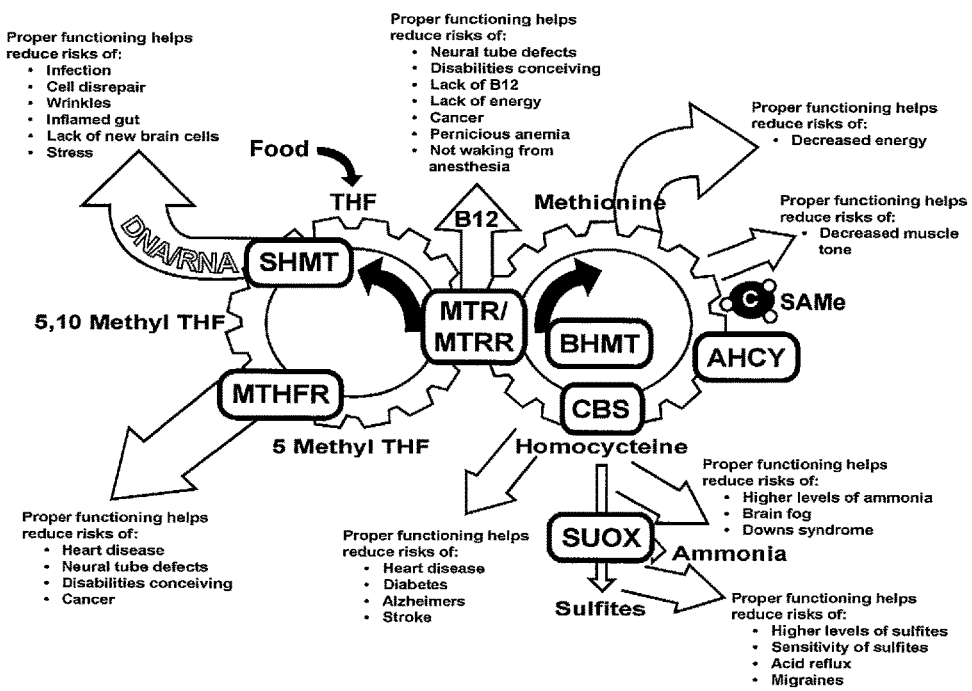

METHODS OF TREATING OPTIC DISORDERS

CROSS REFERENCE TO RELATED APPLICATIONS

This application is a divisional of U.S. patent application Ser. No. 14/459,771 filed Aug. 14, 2014, which a continuation of U.S. application Ser. No. 13/166,207 filed Jun. 22, 2011 which claims the benefit of U.S. Provisional Application No. 61/358,522 filed on Jun. 25, 2010. The disclosure of each of these documents is hereby incorporated in its entirety by reference.

FIELD OF THE INVENTION

The invention relates to methods of treating optic disorders using downstream folate compounds and/or methylcobalamin.

BACKGROUND OF THE INVENTION

Disorders causing visual impairment are numerous. Optic neuropathy is a medical disorder involving visual impairment related to optic nerve damage. The primary symptom of optic neuropathy is vision loss, which is generally bilateral, painless, gradual, and progressive. This vision loss often initially presents as a change in color vision, or dyschromatopsia, and also often begins with a centralized blurring, followed by a progressive decline in visual acuity. The vision loss from optic neuropathy can result in total blindness. Other clinical diagnoses frequently accompany optic neuropathy, including optic nerve head drusen, or accumulations of extracellular material on the optic nerve head, and/or papillitis, or inflammation of the optic nerve head.

There are many forms of optic neuropathy which are generally delineated based upon the cause of the neuropathy. One such form is toxic optic neuropathy, meaning nerve damage resulting from the presence of toxic compounds, such as methanol, ethylene glycol, ethambutol, or certain antibiotics. Another form of optic neuropathy is nutritional optic neuropathy, which is caused by certain nutritional deficiencies. The most common nutritional deficiencies that result in optic neuropathy are B-vitamin deficiencies, such as thiamine, niacin, riboflavin, or folic acid deficiency. (See, e.g., Glaser J S: Nutritional and toxic optic neuropathies. In: Glaser J S, ed., Neuro-ophthalmology. 3rd ed. Philadelphia: Lippincott Williams & Wilkins; 1999: 181-6; Lessell S: Nutritional deficiency and toxic optic neuropathies. In: Albert D M, Jakobiec F A, eds., Principles and Practice of Ophthalmology. 2nd ed. Philadelphia: W. B. Saunders Company; 2000: 4169-76; and Phillips P: Toxic and deficiency optic neuropathies. In: Miller N R, Newman N J, Walsh F B, Hoyt W F, eds., Walsh and Hoyt's Clinical Neuro-ophthalmology. 6th ed. Philadelphia: Lippincott Williams & Wilkins; 2005: 447-63). In cases of nutritional optic neuropathy, the treatment generally employed is to increase the intake of the deficient nutrient. For example, when the optic neuropathy is caused by folic acid deficiency, the disorder can be successfully treated by folic acid supplementation (see, e.g., P. de Silva, et al., Folic acid deficiency optic neuropathy: A case report, Journal of Medical Case Reports 2:299 (2008)).

Retinopathies are another common optic disorder. Retinopathies are disorders that present as non-inflammatory damage to the retina of the eye. Like neuropathies, retinopathies can have numerous causes and are frequently delineated based upon their cause, such as diabetic retinopathy, hypertensive retinopathy, and genetic retinopathy. (Wright, et al., Homocysteine, folates, and the eye, Eye (Land), August 2008, 22(8):989-93, available online Dec. 7, 2007; Abu El-Asrar, et al., Hyperhomocysteinemia and retinal vascular occlusive disease, Eur. J. Ophthalmol., November-December 2002, 12(6):495-500; Becker et al., Epidemiology of homocysteine as a risk factor in diabetes, Metab. Syndr. Relat. Disord., June 2003, 1(2)105-20; Faye A Fishman, The Gale Group Inc., Gale, Detroit, Gale Encyclopedia of Medicine, 2002).

Macular degeneration is yet another common optic disorder. Macular degeneration is an optic disorder characterized by vision loss due to damage to the center of the retina, or macula. This retinal damage is caused by damage to the blood vessels that supply that macula. To a large extent, it is unknown what ultimately causes this blood vessel damage that results in macular degeneration and there is no known treatment for macular degeneration at this time, though vitamin supplements have been suggested to slow the progression of macular degeneration. (Health News, B vitamins may be "silver bullet" for age-related macular degeneration: Daily supplementation with folic acid plus vitamins B6 and B12 may reduce risk of AMD by 35-40 percent, May 2009, 15(5):8-9; Mary Bekker, The Gale Group Inc., Gale, Detroit, Gale Encyclopedia of Nursing and Allied Health, 2002).

Dry Eye Syndrome is still another optic disorder. This disorder, also called Keratoconjunctivitis Sicca (KCS) or Keratitis Sicca, is caused by decreased tear production or increased tear film evaporation. This disorder is usually bilateral and is characterized by dryness and irritation of the eye, frequently getting worse as the day goes on. ("Keratoconjunctivitis Sicca" in The Merck Manual, Home Edition, Merck & Co., Inc., 2003, available at http://www.merck.com/mmhe/sec20/ch230/ch230d.html.).

Folate is a required nutrient and is frequently added to processed foods, such as cereals and breads, in the form of folic acid. However, folic acid is not itself a generally useful form of folate from a metabolic standpoint. Instead, folic acid is converted, through a series of enzymatic steps, to more metabolically active forms of folate via the folate cycle. In the folate cycle, folic acid is first converted into dihydrofolate (DHF) in the presence of vitamin B3. Also with the aid of vitamin B3, DHF is in turn converted into tetrahydrofolate (THF). THF is then converted into 5,10-methylenetetrahydrofolate (5,10-METHF), either directly or via 5-formiminotetrahydrofolate (5FITHF) and 5,10-methenyltetrahydrofolate intermediates. As a part of this same general process, 5-formyltetrahydrofolate (folinic acid), another folate compound, is also converted into 5,10-METHF, again via a 5,10-methenyltetrahydrofolate intermediate. Finally, 5,10-METHF is converted to 5-methyltetrahydrofolate (5MTHF), also called L-methylfolate, levomefolic acid, levomefolate, (6S)-5-methyltetrahydrofolate (6S-5MTHF), which is the predominant metabolically active form of folate. (Hasselwander et al., 5-Methyltetrahydofolate—the active form of folic acid, Functional Foods, 2000 Conference Proceedings, pp 48-59; Kelly et al., Unmetabolized folic acid in serum: acute studies in subjects consuming fortified food and supplements, Am. J. Clin. Nutr., 1997, 65:1790-95).

While this is the ideal path for metabolism of folic acid, as many as 50% of population may have a reduced ability to effectively convert folic acid into its useable form. (Klerk et al., MTHFR 677 C-T polymorphism and risk of coronary heart disease: A Meta-analysis, JAMA, 2002, 288:2023-30).

Because of this, it is possible to have insufficient amounts of metabolically useful folate despite having adequate folic acid intake.

The folate cycle is not isolated, but rather interacts with, and in some cases is intertwined with, other metabolic cycles. For example, the folate cycle interacts with the methylation cycle (also known as the methionine cycle), which produces methionine from homocysteine. More specifically, 5MTHF produced by the folate cycle donates a methyl group which ultimately allows methionine to be produced from homocysteine. Additionally, the folate cycle interacts with the BH4 cycle, which produces tetrahydrobiopterin (BH4) from dihydrobiopterin (BH2). In this case, the interaction between the cycles involves both cycles utilizing a common enzyme: methylenetetrahydrofolatereductase (MTHFr). Because of these complex interactions, malfunctions in one cycle can cause subsequent malfunctions in the other, related cycles. For example, if an individual has a malfunction in the folate cycle such that insufficient 5MTHF is produced, this can cause a buildup of homocysteine and a deficiency of methionine due to an inability of that individual to use the former to produce the latter.

Vitamin B-12 is also intimately linked to the folate cycle. For instance, vitamin B-12 is an important cofactor in the metabolism of intermediate folate compounds, as well as being involved in multiple pathways that utilize L-methylfolate. One example of vitamin B-12's involvement in a pathway that involves L-methylfolate is again in the conversion of homocysteine into methionine. As stated above, 5MTHF donates a methyl group that eventually results in conversion of homocysteine into methionine. That methyl group is transferred from 5MTHF to cobalamin, an unmethylated form of vitamin B-12, thereby producing the methyl form of vitamin B-12, methylcobalamin (also called methyl-B12). Methylcobalamin in turn donates the methyl group to homocysteine to convert it into methionine. Thus, if an individual has an inadequate supply of vitamin B-12, the conversion of homocysteine to methionine will be negatively impacted. Vitamin B-12 is also important in other ways, such as being necessary for nerve repair and nerve health. Because of this, deficiencies in vitamin B-12 and methylcobalamin in particular, can lead to serious complications, such as pernicious anemia.

Because the cycles in which many of these nutrients are involved contain multiple enzymatic steps, they are prone to malfunction. Such malfunction can result, for example, from environmental toxins, ingested chemical compounds or toxins, metabolic imbalances, or genetic polymorphisms in the enzymes which carry out the process steps. For instance, the enzyme MTHFr is involved in the folate cycle. More specifically, this enzyme is at least partially responsible for converting 5,10-METHF into 5MTHF. Mutations in the portion of this enzyme that is involved in this conversion are known to exist. One such mutation, the C677T mutation, is known to slow down the folate cycle activity of this enzyme, resulting in reduced production of 5MTHF from its precursor product(s). For instance, individuals with this particular polymorphism have reduced CNS L-methylfolate. (Surtees et al., Association of cerebrospinal fluid deficiency of 5-methyltetrahydrofolate, but not S-adenosylmethionine, with reduced concentrations of the acid metabolites of 5-hydroxytryptamine and dopamine, Clinical Science, 1994, 86:697-702). Moreover, approximately 70% of patients with diabetic retinopathy have this genetic polymorphism. (Sun et al., The relationship between MTHFR gene polymorphisms, plasma homocysteine levels and diabetic retinopathy in type 2 diabetic meilitus, Chin. Med. J., 2003, 116 (1): 145-7).

MTHFr is also susceptible to mutation in those portions of the enzyme with activities outside the folate cycle. For instance, another function of MTHFr is the conversion of dihydrobiopterin (BH2) to tetrahydrobiopterin (BH4) in the BH4 cycle. BH4 is subsequently involved in multiple other biological pathways and is essential in the synthesis of numerous catecholamines (e.g., dopamine and noradrenaline/norepinephrine) and indolamines (e.g., serotonin and melatonin), as well nitric oxide synthases, which are involved in immune functions as well as vascularization. As such, a mutation in the portion of MTHFr responsible for BH4 cycle activity, such as the A1298C polymorphism, can cause a disruption in the BH4 pathway and subsequent malfunctions in numerous downstream pathways. For example, the A1298C polymorphism has been associated with glaucoma, with higher incidence of cardiovascular disease, and with incidence of eye disease, such as retinopathy. (Shazia et al., MTHFR and A1298C polymorphism and homocysteine levels in primary open angle and primary closed angle glaucoma, Molecular Vision, 2009, 15:2268-2278; Haviv et al., The common mutations C677T and A1298C in the human methylenetetrahydrofolate reductase gene are associated with hyperhomocysteinemia and cardiovascular disease in hemodialysis patients, Nephron, September 2002, 92(1):120-6; Targher et al., Diabetic retinopathy is associated with an increased incidence of cardiovascular events in Type 2 diabetic patients., Diabetic Medicine, 2008, 25:45-50).

Moreover, because these multiple cycles are intricately intertwined, a single malfunction can have far-reaching effects. Anything that breaks down the methylation cycles impacts nitric oxide levels, affects red blood cell function, increases inflammation, causes immune system malfunctions, causes detoxification system malfunctions, causes antioxidant system malfunctions, and negatively impacts our ability to heal and repair. The results of this are reduced blood flow and reduced red blood cells, both of which cause less nutrients and oxygen to get to the eyes; increased inflammation; and reduced detoxification. All of this has been linked to Diabetic retinopathy, Glaucoma, Dry Eyes, Age-related macular degeneration (AMD), branch retinal artery occlusion, a central retinal artery occlusion, a branch retinal vein occlusion, a central vein occlusion, optic neuropathy, and optic neuritis.

Because of the fortification of many processed foods, such as cereals and breads, with folic acid, excessive levels of folic acid may exist in much of the human population. For instance, the U.S. National Academy of Sciences recommends a daily intake of 150-600 .mu.g of folic acid depending on the individual's age and pregnancy status. Many folic acid fortified breakfast cereals supply this amount in a single serving, as do many daily multivitamins. In addition, fortified breads frequently supply 5-10% (or more) of the daily requirement in a single slice, while other fortified grains, such as rice, frequently supply 10-20% (or more) of the daily requirement in a single serving. Because of this, it is very common for an individual to have well over twice, and sometimes upwards of four times, the recommended daily intake of folic acid. (USDA National Nutrient Database for Standard Reference, Release 22, Content of Selected Foods per Common Measure, Folate, DFE sorted by nutrient content).

This is somewhat troubling given that it has been suggested that excessive levels of folic acid might be detrimental in several regards. For instance, some studies have suggested an antagonistic effect of excess folic acid on the metabolically active form by demonstrating an inverse relationship between the amount of unmetabolized folic acid in the blood and the ability of L-methylfolate to cross cell membranes. (Wollack et al., Characterization of folate uptake by choroid plexus epithelial cells in a rat primary culture model, J. Neurochem. 2008; 104:1494-1503; Reynolds, Benefits and risks of folic acid to the nervous system, J. Neurol. Neurosurg. Psychiatry, 2002, 72:567-71).

Further, unmetabolized folic acid has been linked to increased risk of cancer, growth of abnormal cells, increased depression, neurological complications, and decreased immune response. (Troem et al., Unmetabolized Folic Acid in Plasma Is Associated with Reduced Natural Killer Cell Cytotoxicity among Postmenopausal Women, J. Nutr., 2006, 136:189-194; Smith et al., Pteridines and mono-amines: relevance to neurological damage, Postgrad. Med. J., 1986, 62(724):113-23; Asien et al., High-dose B vitamin supplementation and cognitive decline in Alzheimer disease: a randomized controlled trial, JAMA, 2008, 300(15):1774-83). The presence of unmetabolized folic acid in the body has not heretofore been linked with pathological conditions of the eye. However, active folate and active vitamin B-12 have been found to improve corneal nerve fiber density (CNFD) and branch density, for example in patients with diabetic neuropathies. (Quattrini et al., Surrogate Markers of Small Fiber Damage in Human Diabetic Neuropathy, Diabetes, 2007, 56(8):2148-54).

SUMMARY OF THE INVENTION

The present invention is directed toward methods of treating optic disorders using downstream folate compounds and, optionally, methylcobalamin. One aspect of the present invention is a method of improving or alleviating an optic disorder or the symptoms related thereto in a non-folic acid-deficient subject organism, the method comprising a) identifying a non-folic acid-deficient subject organism suffering from an optic neuropathy, and b) administering to the subject organism an effective amount of one or more downstream folate compounds. In other aspects, the invention further involves c) decreasing the subject organism's intake of folic acid.

In certain embodiments of the present invention, the subject organism is a human. In other embodiments, the one or more downstream folate compounds are selected from the group consisting of DHF, THF, 5FlTHF, 5,10-METHF, and L-methylfolate. In particular embodiments, the downstream folate compounds comprise L-methylfolate. In other particular embodiments, the L-methylfolate is provided in a dose of 1 mcg-25 mg/day. In other embodiments, the L-methylfolate is provided in a dose of 1-25 mg/day.

Another aspect of the present invention is a method of improving visual acuity in a subject organism, the method comprising 1) identifying a non-folic acid-deficient subject organism with a) reduced visual acuity, b) an optic disorder which can cause reduced visual acuity, and c) a malfunction in one or more of the folate cycle and BH4 cycle; and 2) administering to the subject organism an effective amount of one or more downstream folate compounds to improve the subject organism's visual acuity. In other aspects, the invention further involves 3) decreasing the subject organism's intake of folic acid.

In certain embodiments of the present invention, the malfunction in one or more of the folate cycle and BH4 cycle is one or more of the C677T and A1298C mutations.

In certain other embodiments, the subject organism possesses both of the C677T and A1298C mutations. In still further embodiments, the optic disorder is selected from the group consisting of optic neuropathy, retinopathy, macular degeneration, or optic atrophy. In yet other embodiments, the subject organism is a human. In still further embodiments, the one or more downstream folate compounds are selected from the group consisting of DHF, THF, 5FlTHF, 5,10-METHF, and L-methylfolate. In certain embodiments, the downstream folate compounds comprise L-methylfolate. In particular embodiments, the L-methylfolate is provided in a dose of 1-25 mg/day.

Yet another aspect of the present invention is a method of improving visual acuity in a subject organism, the method comprising 1) identifying a subject organism with a) reduced visual acuity, b) an optic disorder which can cause reduced visual acuity, c) a malfunction in one or more of the folate cycle and BH4 cycle, d) above normal homocysteine levels, and e) deficiencies in vitamin B-12 and vitamin D; and 2) administering to the subject organism an effective amount of one or more downstream folate compounds and methyl-B12. In other aspects, the invention further involves 3) decreasing the subject organism's intake of folic acid In yet other aspects, the invention further involves administering an effective amount of one or both of vitamin B6 and vitamin D3.

In certain embodiments of the present invention, the malfunction in one or more of the folate cycle and BH4 cycle is one or more of the C677T and A1298C mutations. In certain other embodiments, the subject organism possesses both of the C677T and A1298C mutations. In still further embodiments, the optic disorder is selected from the group consisting of optic neuropathy, retinopathy, macular degeneration, or optic atrophy. In yet other embodiments, the subject organism is a human. In still further embodiments, the one or more downstream folate compounds are selected from the group consisting of DHF, THF, 5FlTHF, 5,10-METHF, and L-methylfolate. In certain embodiments, the downstream folate compounds comprise L-methylfolate. In particular embodiments, the L-methylfolate is provided in a dose of 1-25 mg/day.

In other particular embodiments, the methyl-B12 is administered in a dose of 1-2.5 mg/day.

BRIEF DESCRIPTION OF THE DRAWINGS

FIG. 1 shows the major steps and intermediates involved in the folate cycle and the interaction of the folate cycle with the methionine cycle.

DESCRIPTION OF THE INVENTION

The present invention springs, in part, from the inventor's surprising demonstration of the successful treatment of several optic disorders using folate, optionally in combination with one or more of methyl-B12, vitamin B6, and vitamin D3, in patients who possessed some type of metabolic abnormality associated with folic acid metabolism or intertwined metabolic cycles. The inventor has successfully treated individuals with neuropathies, retinopathies, macular degeneration, and associated ocular pathologies by administering one or more downstream folate compounds and, optionally, one or more of methyl-B12, vitamin B6, vitamin D3, and reduced folic acid intake.

The present invention thus relates to methods of treating optic disorders or reducing or alleviating the signs, symptoms, or pathological conditions related to such optic disorders. In certain embodiments, the invention relates to methods of treating optic disorders using downstream folate compounds to negate the occurrence of environmental, medication, lifestyle, disease, or genetically induced interference and/or disruption in specific biochemical reactions necessary for normal vision. In certain embodiments, methods are provided for treating optic disorders, or reducing the symptoms thereof, the methods involving the administration of one or more downstream folate compounds. In one particular embodiment, the method comprises administration of L-methylfolate. In other embodiments, the method further involves reducing dietary intake of folic acid. In certain other embodiments, the method further involves administering methyl-B12. In still further embodiments, the method further comprises administering one or more of vitamin B6 and vitamin D3. In still other embodiments, the method further involves first identifying a subject organism with an optic disorder which individual is not folic acid deficient. In still further embodiments, the method involves identifying a subject organism with a malfunction in one or more of the folate or B4 cycles. In certain embodiments, such a malfunction is one or more of the C677T and A1298C mutations. In still further embodiments, the method further involves identifying a subject who is vitamin B12 and D3 deficient and who has elevated levels of homocysteine. In other embodiments, the method involves identifying a subject organism which is not folic acid deficient.

The entire contents of all references cited in this disclosure are specifically incorporated by reference herein. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In this disclosure, a number of terms and abbreviations are used. The following definitions are provided.

As used herein, "comprising" is to be interpreted as specifying the presence of the stated features, integers, steps, reagents, or components as referred to, but does not preclude the presence or addition of one or more features, integers, steps or components, or groups thereof. Thus, for example, a composition comprising one downstream folate compound may comprise more downstream folate compounds than those actually recited, i.e., it may comprise two or more distinct downstream folate compounds. Additionally, the term "comprising" is intended to include embodiments encompassed by the terms "consisting essentially of" and "consisting of". Similarly, the term "consisting essentially of" is intended to include embodiments encompassed by the term "consisting of".

In certain embodiments, the term "about," when used in conjunction with a numerical variable, limitation, or range means plus or minus 5%. In other embodiments, the term "about," when used in conjunction with a numerical variable, limitation, or range means plus or minus 1%.

The term "downstream folate compound" or "downstream folate" means a folate compound downstream of folic acid in the folate cycle. The "folate cycle" refers to the process by which metabolically unrecognizable/inactive folates are converted into metabolically useful/recognizable/active folates in the body. FIG. 1 shows the major steps and intermediates involved in the folate cycle. As can be seen, during the folate cycle, folic acid is first converted into dihydrofolate (DHF), which is in turn converted to tetrahydrofolate (THF). THF is then converted into 5,10-methylenetetrahydrofolate (5,10-METHF), either directly or via 5-formiminotetrahydrofolate (5FITHF) and 5,10-methenyltetrahydrofolate intermediates. As a part of this same general process, 5-formyltetrahydrofolate (folinic acid), another folate compound, is also converted into 5,10-METHF, again via a 5,10-methenyltetrahydrofolate intermediate. 5,10-METHF is then converted to 5-methyltetrahydrofolate (5MTHF), also called L-methylfolate, levomefolic acid, levomefolate, (6S)-5-methyltetrahydrofolate (6S-5MTHF), which is the predominant metabolically active form of folate. L-methylfolate is also referred to at various times and/or by various pharmaceutical manufacturers as L-5-Methyltetrahydrofolate, L-5-MTHF, and L-MTHF. The enzyme methylenetetrahydrofolatereductase (MTHFr) is at least partially responsible for converting 5,10-METHF into 5MTHF. Thus, folate compounds downstream of folic acid in the folate cycle include DHF, THF, 5FITHF, 5,10-methenyltetrahydrofolate, 5,10-METHF, and L-methylfolate. Downstream folate compounds are included, for example, in certain commercially available dietary supplements, including, but not limited to, Metafolin® available from Merck; CerefolinNAC®, Deplin®, and Metanx® available from Pamlab; and Quatrefolic® available from Gnosis.

As used herein, the term "BH4 cycle" means the cycle responsible for the conversion of dihydrobiopterin (BH2) to tetrahydrobiopterin (BH4). One enzyme involved in this cycle is MTHFr.

As used herein, "methyl-B12" refers to methylcobalamin.

As used herein, a "malfunction" in the folate or BH4 cycle means an exogenous or endogenous condition which negatively affects the normal operation of the folate cycle and/or BH4 cycle. Such malfunctions could result, for example, from environmental toxins, ingested chemical compounds or toxins, metabolic imbalances, or genetic disorders or mutations affecting enzymes in the folate and/or BH4 cycle, including the C677T and/or A1298C genetic mutations.

As used herein, "C677T" refers to a mutation in one or more alleles of a gene encoding the MTHFr enzyme where the cytosine nucleotide at nucleotide position 677 of the MTHFr gene is replaced with a thymine nucleotide. This mutation results in a malfunction in the enzyme's folate cycle activity.

As used herein, "A1298C" refers to a mutation in one or more alleles of a gene encoding the MTHFr enzyme where the adenine nucleotide at nucleotide position 1298 of the MTHFr gene is replaced with a cytosine nucleotide. This mutation results in a malfunction in the enzyme's BH4 cycle activity.

As used herein, "optic disorder" means a disorder or malfunction which results in physical disease or a pathological condition of the eye or related structures, such as drusen, papillitis, optic neuropathy, retinopathy, or vitreous hemorrhage; and/or other vision-related signs or symptoms, such as reduced visual acuity, optic field defect, or vision related headaches. Optic disorders include toxic optic neuropathy, nutritional optic neuropathy, viral optic neuropathy, hypertension retinopathy, diabetic retinopathy, macular degeneration, optic atrophy, and optic nerve inflammation. "Toxic optic neuropathy" as used herein can include optic neuropathy resulting from toxic amounts of unmetabolized folic acid that have accumulated in an individual, such as an individual who is impaired in metabolizing folic acid to downstream folate compounds. In addition, "toxic optic neuropathy" can include optic neuropathy resulting from toxic amounts of cyanocobalamin, a form of vitamin B-12 commonly found in dietary supplements, that have accumulated in an individual, such as an individual who is impaired in the ability to metabolize cyanocobalamin or to convert it into other forms of vitamin B-12, such as methyl-B12.

"Visual acuity" refers to the clarity and/or sharpness of the subject organism's vision. "Reduced visual acuity" means a visual acuity below what is generally accepted as normal or typical for that particular subject organism. For example, in an adult human, reduced visual acuity would include visual acuity less than 20/20, e.g., 20/40 vision.

The term "non-folic acid-deficient" means a subject organism that has been found to not have a deficiency in folic acid, i.e., in folic acid as provided in the diet or through dietary supplementation, and as measured in the blood serum following such intake. A determination that a subject organism does not have a folic acid deficiency can be made by any number of suitable tests or analyses to determine folic acid or folate levels in the body. Such tests are well known to persons of ordinary skill in the art and include analysis of folic acid levels in the blood plasma and/or analysis of folic acid levels within red blood cells. In addition, a determination that a subject organism does not have a folic acid deficiency can be made through an analysis of a subject organism's dietary intake of folic acid. If such an analysis reveals that an adequate amount of folic acid is being consumed through the diet, then the subject organism is non-folic acid-deficient. For example, a non-folic acid-deficient subject includes a person who consumes at least the appropriate recommended daily allowance of folic acid as established by the U.S. National Academy of Sciences. In contrast, a folic acid deficient individual would include a person known to consume far below the recommended daily allowance of folic acid.

As used herein, a nutritional "deficiency," such as a deficiency in vitamin B-12, methyl-B12, vitamin D3, or vitamin B6, means the subject organism possesses a level of the nutrient of interest that is less than the level that is generally accepted as normal by persons of ordinary skill in the art. Such levels are well known to persons of ordinary skill in the art, as are methods for determining a particular subject organism's levels of nutrients of interest. Methods of testing include blood tests for nutrients of interest.

As used herein, "subject organism" means any animal, regardless of species, gender, or age, capable of meeting the other criteria of the invention (e.g., non-folic acid-deficient with an optic neuropathy). In certain embodiments, the subject organism is a mammal. In certain other embodiments, the subject organism is a companion animal, preferably a dog, cat, horse, or bird. In other embodiments, the subject organism is a human.

As used herein, an "effective amount" is an amount of a compound, such as a downstream folate compound, methyl-B12, vitamin B6, or vitamin D3, that is sufficient to cause favorable changes in the subject organism's optic disorder. For instance, an effective amount of downstream folate includes a sufficient amount of a downstream folate compound to cause improved visual acuity when provided regularly over a period of days to years. An effective amount similarly includes a sufficient amount of a downstream folate compound to cause reduced drusen and/or papillitis when provided regularly over a period of days to years.

In certain embodiments, an effective amount of a downstream folate compound is about 1 mcg-25 mg per day, about 1-20 mg per day, about 2.8-15 mg per day, or about 5-10 mg per day. In other embodiments, an effective amount of a downstream folate compound is about 1 mcg per day, about 10 mcg per day, about 20 mcg per day, about 30 mcg per day, about 40 mcg per day, about 50 mcg per day, about 60 mcg per day, about 70 mcg per day, about 80 mcg per day, about 90 mcg per day, about 100 mcg per day, about 200 mcg per day, about 300 mcg per day, about 400 mcg per day, about 500 mcg per day, about 600 mcg per day, about 700 mcg per day, about 800 mcg per day, about 900 mg per day, about 1 mg per day about 1.5 mg per day, about 2 mg per day, about 2.5 mg per day, about 2.8 mg per day, about 3 mg per day, about 3.5 mg per day, about 4 mg per day, about 4.5 mg per day, about 5 mg per day, about 6 mg per day, about 7 mg per day, about 7.5 mg per day, about 8 mg per day, about 9 mg per day, about 10 mg per day, about 11 mg per day, about 12 mg per day, about 13 mg per day, about 14 mg per day, about 15 mg per day, about 16 mg per day, about 17 mg per day, about 18 mg per day, about 19 mg per day, about 20 mg per day, about 21 mg per day, about 22 mg per day, about 23 mg per day, about 24 mg per day, or about 25 mg per day. In certain other embodiments, an effective amount of a downstream folate compound is about 10 mcg-200 mg per week, about 100 mcg-200 mg per week, about 1-200 mg per week, about 5-150 mg per week, about 10-125 mg per week, about 19.6-105 mg per week, about 20-100 mg per week, about 25-90 mg per week, about 30-80 mg per week, about 35-70 mg per week, about 40-60 mg per week, or about 50-55 mg per week. In other embodiments, an effective amount of a downstream folate compound is about 5-1000 mg per month, about 20-900 mg per month, about 40-800 mg per month, about 50-700 mg per month, about 60-600 mg per month, about 80-500 mg per month, about 100-400 mg per month, about 150-300 mg per month, or about 200-250 mg per month.

In certain embodiments, an effective amount of methyl-B12 is about 1 mcg to about 10 mg per day, about 0.5-5 mg per day, or about 1-2.5 mg per day. In other embodiments, an effective amount of methyl-B12 is about 0.5-100 mg per week, about 3-35 mg per week, or about 7-17.5 mg per week. In other embodiments, an effective amount of methyl-B12 is about 2-300 mg per month, about 15-150 mg per month, or about 30-75 mg per month.

In other embodiments, multiple compounds are administered, such as folate and methyl-B12, or folate, methyl-B12 and one or more of vitamin B6 and D3. In such cases, an effective amount of each component is an amount sufficient to cause favorable changes in the subject organism's optic disorder when the components are administered in the desired combination.

It should also be noted that these amounts do not need to be supplied in a single dose, but rather can be supplied in multiple daily, weekly, or monthly doses. For example, dosages can be 1 time per day, 2 times per day, 3 times per day, 4 times per day, 5 times per day, 6 times per day, 7 times per day, 1 time per week, 2 times per week, 3 times per week, 4 times per week, 5 times per week, 6 times per week, 7 times per week, 1 time per month, 2 times per month, 3 times per month, 4 times per month, 5 times per month, 6 times per month, 7 times per month, 8 times per month, 9 times per month, 10 times per month, 11 times per month, 12 times per month, 13 times per month, 14 times per month, 15 times per month, 16 times per month, 17 times per month, 18 times per month, 19 times per month, 20 times per month, 21 times per month, 22 times per month, 23 times per month, 24 times per month, 25 times per month, 26 times per month, 27 times per month, 28 times per month, 29 times per month, 30 times per month, or 31 times per month.

In addition, the administration of the effective amount of one or more downstream folate compounds can continue for a period of days to years. For instance, in certain embodiments, the downstream folate compound(s) are administered on a regular basis for at least 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 2 months, 3 months, 4 months, 5 months, 6 months, 7 months, 8 months, 9 months, 10 months, 11 months, 12 months, 13 months, 14 months, 15 months, 16 months, 17 months 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or the remaining duration of the subject organism's life. In other embodiments, the downstream folate compound(s) are administered on a regular basis for less than 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 2 months, 3 months, 4 months, 5 months, 6 months, 7 months, 8 months, 9 months, 10 months, 11 months, 12 months, 13 months, 14 months, 15 months, 16 months, 17 months 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or the remaining duration of the subject organism's life.

The compounds being administered can be supplied in any form and by any route known in the art, for example, orally (e.g., tablet, capsule, liquid, oral suspension, etc.), transdermally (e.g., ointment, patch, etc.), sublingually, subcutaneously, intramuscularly, rectally, in drop form, or intravenously. In certain other embodiments, oral doses can be provided in a time release or extended release form.

Methyl-B12 is available from numerous sources, such as Source Naturals, which supplies methyl-B12, for example, in 5 mg sublingual doses. In certain embodiments, the method of the present invention involves administering a composition containing 7.5-15 mg L-methylfolate. In still other embodiments, the method of the present invention involves administering a composition containing 5.6 mg L-methylfolate, 2 mg methylcobalamin, and 600 mg N-acetylcysteine. In certain other embodiments, the method of the present invention involves administering a composition containing 3 mg L-methylfolate, 35 mg pyridoxal 5'-phosphate (an active form of vitamin B6), and 2 mg methylcobalamin (methyl-B12).

The present invention involves treatment of subject organisms for optic disorders using one or more downstream folate compounds and/or methyl-B12, and, optionally, one or more of vitamin B6 and vitamin D3. The present inventor has unexpectedly found that optic disorders, such as optic neuropathies, can be effectively treated, or the symptoms thereof can be effectively reduced, by administering to those subject organisms an effective amount of one or more downstream folate compounds and methyl-B12, either individually or in combination, and optionally in combination with one or more of vitamin B6 and vitamin D3.

To identify subject organisms with optic disorders, some form of examination and/or testing is typically performed. Such testing is well known to persons of ordinary skill in the art and can include a complete eye exam, including visual field analysis, retinal photographs, and/or laser scanning. In addition, a determination as to whether the subject organism is non-folic acid-deficient can optionally be made through either testing/analysis or review of dietary folic acid intake, as described above.

In certain embodiments, testing or other analysis is done to determine whether the subject organism possesses some form of malfunction in the folate and/or BH4 cycles. Such testing is well known to persons of ordinary skill in the art and includes genetic testing to determine the presence or absence of one or both of the C677T and A1298C mutations.

Useful testing to determine whether the subject organism possesses some form of malfunction in the folate and/or BH4 cycles also includes a test to determine if the subject organism possesses elevated levels of homocysteine, as excess homocysteine can be indicative of a malfunction in the folate cycle due to the interaction between the methionine and folate cycles. Such tests are well known to persons of ordinary skill in the art and include a homocysteine blood test. Another useful test which can be employed is a test to determine whether the subject organism possesses levels of vitamin B-12 that are within the normal range. In addition to determining whether an individual is vitamin B-12 deficient, such a test is useful, for example, to determine the cause of the elevated homocysteine levels, since elevated homocysteine can also result from a vitamin B-12 deficiency, as vitamin B-12 is also involved in the conversion of homocysteine to methionine. Such tests are well known to persons of ordinary skill in the art and include a vitamin B-12 blood test. In certain preferred embodiments, a homocysteine blood test will be performed along with a vitamin B-12 blood test and an analysis of the subject organism's dietary folate intake to determine whether the subject organism 1) consumes adequate folic acid, and therefore is not folic acid deficient, 2) has vitamin B-12 levels that are within the normal range, and therefore is not vitamin B-12 deficient, and 3) possesses excess homocysteine, and therefore, in light of the results of 1) and 2), appears to have a malfunction in the folate pathway. Testing can also be done to determine if the subject organism is vitamin D deficient, such as a 25-hydroxy vitamin D blood test.

Treatment of a non-folic acid-deficient subject organism according to the present invention is accomplished by supplying that subject organism with an effective amount of one or more downstream folate compounds. As described above, such compounds can include one or more of DHF, THF, 5FITHF, 5,10-METHF, and L-methylfolate. Also as discussed above, the downstream folate compound(s) can be administered in one or more doses at regular intervals for a period of days to years.

In addition to administering downstream folate compound(s), in certain embodiments, the method further involves reducing the subject organism's folic acid intake. Such a reduction in intake can be accomplished in any suitable manner. Methods for reducing folic acid intake are well known to persons of ordinary skill in the art and include reducing the amount of folic acid consumed through dietary supplements and/or reducing the intake of folic acid fortified foods, such as processed foods, including fortified breads and cereals.

In one particular embodiment, the method involves identifying a non-folic acid-deficient person suffering from an optic neuropathy, and a) administering to that person 1 mcg to 25 mg per day of L-methylfolate, and b) decreasing the person's intake of folic acid.

In another particular embodiment the method involves 1) identifying a non-folic acid-deficient person with a) reduced visual acuity, b) an optic disorder selected from the group consisting of neuropathy, retinopathy, macular degeneration, or atrophy, and c) one or both of the C677T and A1298C mutations; and 2) a) administering to that person 1-25 mg per day of L-methylfolate, and b) decreasing the person's intake of folic acid. In certain particular embodiments, folic acid intake is decreased by 1-4 mg per day.

In other embodiments, the method involves administering methyl-B12. In certain embodiments, the methyl-B12 is administered in an amount of 1-2.5 mg per day. In certain embodiments an effective amount of methyl-B12 is administered alone to treat an optic disorder. In certain other embodiments, the methyl-B12 is administered in conjunction with a downstream folate compound. In still further embodiments, folate and methyl-B12 are administered in conjunction with one or more of vitamin B6 and vitamin D3.

In certain preferred embodiments, the method involves 1) identifying a subject organism with an optic disorder; 2) testing the subject organism to determine if it possesses one or both of the C677T and A1298C polymorphisms; 3) testing the subject organism to determine if it possesses above normal homocysteine levels and below normal vitamin B12 and vitamin D levels; and) administering to the subject organism an effective amount of a downstream folate compound and methyl-B12 and, optionally, one or more of vitamin B6 and vitamin D3.

Following treatment, the effectiveness of the treatment can be determined by again administering some form of testing or examination to determine the presence and/or severity of pathological condition(s) and/or symptom(s) wherein a reduction in the presence and severity of pathological condition(s) and/or symptom(s) indicates that the treatment method was effective. Such a reduction in the presence and/or severity of pathological condition(s) and/or symptoms can be readily determined by persons of ordinary skill in the art and includes improved visual acuity, improved field defect, reduced headaches, reduced drusen, and reduced papillitis.

EXAMPLES

The present invention is further defined in the following Examples. It should be understood that these Examples, while indicating preferred embodiments of the invention, are given by way of illustration only.

Example 1

Patient 1 was a 32-year-old white female who presented with headaches, blurred vision, and a visual acuity of 20/50. A detailed dietary history indicated that she was not at risk for folic acid deficiency. She was evaluated medically and diagnosed as having optic nerve head drusen and toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 30 days, she was reexamined and found to no longer have the above-described symptoms and to have a normal visual acuity of 20/20.

Example 2

Patient 2 was a 16-year-old white female who presented with headaches, blurred vision, and a visual acuity of 20/30. A detailed dietary history indicated that she was not at risk for folic acid deficiency. She was evaluated medically and diagnosed as having toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 60 days, she was reexamined and found to no longer have the above-described symptoms and to have a normal visual acuity of 20/20.

Example 3

Patient 3 was an 8-year-old white male who presented with headaches, loss of vision, and a visual acuity of 20/40. A detailed dietary history indicated that he was not at risk for folic acid deficiency. He was evaluated medically and diagnosed as having papillitis and toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 30 days, he was reexamined and found to no longer have the above-described symptoms and to have a normal visual acuity of 20/20.

Example 4

Patient 4 was a 19-year-old white male who presented with headaches, loss of vision, visual field loss, and a visual acuity of 20/80. A detailed dietary history indicated that he was not at risk for folic acid deficiency. He was evaluated medically and diagnosed as having buried optic nerve head drusen and toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 6 months, he was reexamined and found to no longer have the above-described symptoms and to have a normal visual acuity of 20/20.

Example 6

Patient 5 was a 34-year-old white female who presented with headaches, loss of vision, visual field loss, and a visual acuity of 20/60. A detailed dietary history indicated that she was not at risk for folic acid deficiency. She was evaluated medically and diagnosed as having papillitis. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 30 days, she was reexamined and found to no longer have the above-described symptoms and to have a normal visual acuity of 20/20.

Example 6

Patient 6 was an 11-year-old white female who presented with headaches, visual field defect, and a reduced visual acuity of 20/40. A detailed dietary history indicated that she was not at risk for folic acid deficiency. She was evaluated medically and diagnosed as having papillitis and toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 30 days, she was reexamined and found to no longer have the above-described symptoms and to have a normal visual acuity of 20/20.

Example 7

Patient 7 was a 9-year-old white female who presented with headaches, visual field defect, and a reduced visual acuity of 20/40. A detailed dietary history indicated that she was not at risk for folic acid deficiency. She was evaluated medically and diagnosed as having papillitis and buried drusen. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 6 months, she was reexamined and found to no longer have the above-described symptoms and to have a normal visual acuity of 20/20.

Example 8

Patient 8 was a 51-year-old white female who presented with headaches, visual field defect, and a reduced visual acuity of 20/200. A detailed dietary history indicated that she was not at risk for folic acid deficiency. She was evaluated medically and diagnosed as having ischemic optic neuropathy. Previously she had been twice diagnosed as having an unknown and untreatable eye disorder that would progress to the point of blindness. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After one year, she was reexamined and found to no longer have the above-described symptoms and to have a normal visual acuity of 20/20.

Example 9

Patient 9 was a 20-year-old white female who presented with migraine headaches, visual field defect, and a visual acuity of 20/50. A detailed dietary history indicated that she was not at risk for folic acid deficiency. She had been previously diagnosed as having papillitis. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 6 months, she was reexamined and found to no longer have the above-described symptoms and to have a normal visual acuity of 20/20.

Example 10

Patient 10 was a 31-year-old white female who presented with visual field defect and a visual acuity of 20/60. A detailed dietary history indicated that she was not at risk for folk acid deficiency. She was evaluated medically and diagnosed as having toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 3 months, she was reexamined and found to no longer have the above-described symptoms and to have a normal visual acuity of 20/20.

Example 11

Patient 11 was a 60-year-old white male who presented with major visual field defect and a visual acuity of 20/200. Patient 11 had a visually acuity that qualified as legally blind for 53 years. A detailed dietary history indicated that he was not at risk for folic acid deficiency. He had been diagnosed as having optic atrophy at age 7. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8-15 mg L-methylfolate and 1-2.5 mg methyl-B12 per day, in addition to vitamin B6 and D3 supplements, and told to reduce intake of processed foods as much as possible, such as by switching to organic foods. After 3 months, he was reexamined and found to have improved performance on all tests administered and to have a greatly improved visual acuity of 20/40.

Example 12

Patient 12 was a 68-year-old male who presented with a visual acuity of 20/100. A detailed dietary history indicated that he was not at risk for folic acid deficiency. He was evaluated medically and diagnosed as having hypertension retinopathy resulting in detachment. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 7.5 mg L-methylfolate and 1-2.5 mg methyl-B12 per day, in addition to vitamin B6 and D3 supplements, and told to reduce intake of processed foods as much as possible, such as by switching to organic foods. After 6 months, he was reexamined and found to have an improved visual acuity of 20/25.

Example 13

Patient 13 was a 75-year-old female who presented with a visual acuity of 20/70. A detailed dietary history indicated that she was not at risk for folic acid deficiency. She was evaluated medically and diagnosed as having diabetic retinopathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 7.5 mg L-methylfolate and 1-2.5 mg methyl-B12 per day, in addition to vitamin B6 and D3 supplements, and told to reduce intake of processed foods as much as possible, such as by switching to organic foods. After 30 days, she was reexamined and found to have a greatly improved visual acuity of 20/30.

Example 14

Patient 14 was a 20-year-old female who presented with a visual acuity of 20/50. A detailed dietary history indicated that she was not at risk for folic acid deficiency. She was evaluated medically and diagnosed as having toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8 mg L-methylfolate and 1-2.5 mg methyl-B12 per day, in addition to vitamin B6 and D3 supplements, and told to reduce intake of processed foods as much as possible, such as by switching to organic foods. After 30 days, she was reexamined and found to have a normal visual acuity of 20/20.

Example 15

Patient 15 was a 16 year old male who presented with a visual acuity of 20/100 and 20/60 in the right and left eyes, respectively. A detailed dietary history indicated that he was not at risk for folic acid deficiency. He was evaluated medically and diagnosed as having viral optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 7.5 mg L-methylfolate and 1-2.5 mg methyl-B12 per day, in addition to vitamin B6 and D3 supplements, and told to reduce intake of processed foods as much as possible, such as by switching to organic foods. After one year, he was reexamined and found to have a greatly improved visual acuity of 20/40 and 20/30 in the right and left eyes, respectively.

Example 16

Patient 16 was a 60-year-old female who presented with a visual acuity of 20/30 and 20/200 in the right and left eyes, respectively. A detailed dietary history indicated that she was not at risk for folic acid deficiency. She was evaluated medically and diagnosed as having vitreous hemorrhage, hypertension, and diabetes. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 15 mg L-methylfolate and 1-2.5 mg methyl-B12 per day, in addition to vitamin B6 and D3 supplements, and told to reduce intake of processed foods as much as possible, such as by switching to organic foods. After 60 days, she was reexamined and found to have a normal visual acuity of 20/20 in both eyes.

Example 17

Patient 17 was a 7-year-old male who presented with a visual acuity of 20/30 and 20/25 in the right and left eyes, respectively. A detailed dietary history indicated that he was not at risk for folic acid deficiency. He was evaluated medically and diagnosed as having toxic optic neuropathy. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 2.8 mg L-methylfolate and 1-2.5 mg methyl-B12 per day, in addition to vitamin B6 and D3 supplements, and told to reduce intake of processed foods as much as possible, such as by switching to organic foods. After 60 days, he was reexamined and found to have a normal visual acuity of 20/20 in both eyes.

Example 18

Patient 18 was a 17-year-old male who presented with a visual acuity of 20/60 and 20/50 in the right and left eyes, respectively. A detailed dietary history indicated that he was not at risk for folic acid deficiency. He was evaluated medically and diagnosed as having macular degeneration. In addition, through various blood tests, it was determined that this patient had higher than normal levels of homocysteine and below normal levels of vitamin B-12 and 25-hydroxy vitamin D. In addition, through genetic testing it was determined that the patient had one or both of the C677T and A1298C polymorphisms. The patient was placed on a regimen of 7.5 mg L-methylfolate and 1-2.5 mg methyl-B12 per day, in addition to vitamin B6 and 10,000 IU vitamin D3 supplements, and told to reduce intake of processed foods as much as possible, such as by switching to organic foods. After 60 days, he was reexamined and found to have a greatly improved visual acuity of 20/30 and 20/25 in the right and left eyes, respectively.

Example 19

A population of approximately 200 individual patients of mixed race and gender ranging in age from 3-80 years old, each with an optic disorder, was collected. Each patient was evaluated using a complete eye exam including visual field analyses, retinal photographs, laser scanning and ultra sound to determine presence, type, and severity of the optic disorder. The optic disorders present in the study included toxic optic neuropathy, buried optic nerve head drusen, surfaced optic nerve head drusen, papillitis, ischemic optic neuropathy, age-related macular degeneration, retinal hemorrhage (hypertensive and diabetic), and vitreous hemorrhage.

Through various blood tests, it was determined that each patient had one or more of higher than normal levels of homocysteine, below normal levels of vitamin B-12, and below normal levels of 25-hydroxy vitamin D. In addition, through genetic testing it was determined that each patient had one or both of the C677T and A1298C polymorphisms. Following initial testing, each patient was placed on a regimen of 1-15 mg L-methylfolate and 1-2.5 mg methyl-B12 per day, as well as supplemental vitamin B6 and D3, all supplied either in a single dose or multiple doses. Each patient was also told to reduce intake of processed foods as much as possible, such as by switching to organic alternatives. The amount of folate administered was reduced for individuals who successfully reduced their folic acid intake and was increased for individuals who did not successfully reduce folic acid intake. Every 30 days, each patient was reexamined/reevaluated to determine the effectiveness of the treatment.

In approximately 50% of the patient population, improved visual acuity was found to exist within 30 days; in approximately 75% of the patient population, improved visual acuity was found to exist within 60 days; in approximately 95% of the patient population, improved visual acuity was found to exist within 6 months; and in approximately 100% of the patient population, improved visual acuity was found to exist within 1 year.

The present invention is not limited to the embodiments described and exemplified above, but is capable of variation and modification.

The invention claimed is:

1. A method of improving visual acuity in a non-folic acid-deficient subject organism suffering from an optic disorder and reduced visual acuity, the method comprising administering to the subject organism an effective amount of one or more compounds containing folate found downstream of folic acid in the folate cycle to improve the subject organism's visual acuity, wherein the subject organism comprises one or more of the C677T and A1298C mutations.

2. The method of claim 1, wherein the subject organism possesses both of the C677T and A1298C mutations.

3. The method of claim 1, wherein the optic disorder is selected from the group consisting of optic neuropathy, retinopathy, macular degeneration, or optic atrophy.

4. The method of claim 3, wherein the subject organism is a human.

5. The method of claim 1, further comprising decreasing the subject organism's intake of folic acid.

6. The method of claim 1, wherein the one or more compounds containing folate found downstream of folic acid in the folate cycle are selected from the group consisting of 5-formyltetrahydrofolate, DHF, THF, 5FlTHF, 5,10-METHF, and L-methylfolate.

7. The method of claim 6, wherein the one or more compounds containing folate found downstream of folic acid in the folate cycle comprise L-methylfolate.

8. The method of claim 7, wherein the L-methylfolate is provided in a dose of 1 mcg to 25 mg/day.

9. A method of improving visual acuity in a subject organism suffering from an optic disorder and reduced visual acuity, the method comprising administering to the subject organism an effective amount of one or more compounds containing folate found downstream of folic acid in the folate cycle and methyl-B12, wherein the subject organism has (a) one or more of the C677T and A1298C mutations, (b) above normal homocysteine levels, and (c) deficiencies in vitamin B-12 and vitamin D.

10. The method of claim 9, wherein the optic disorder is selected from the group consisting of optic neuropathy, retinopathy, macular degeneration, or optic atrophy.

11. The method of claim 10, wherein the subject organism is a human.

12. The method of claim 9, further comprising decreasing the subject organism's intake of folic acid.

13. The method of claim 9, wherein the one or more compounds containing folate found downstream of folic acid in the folate cycle are selected from the group consisting of 5-formyltetrahydrofolate, DHF, THF, 5FlTHF, 5,10-METHF, and L-methylfolate.

14. The method of claim 13, wherein the one or more compounds containing folate found downstream of folic acid in the folate cycle comprise L-methylfolate.

15. The method of claim 14, wherein the L-methylfolate is provided in a dose of 1 mcg 25 mg/day.

16. The method of claim 9, wherein the methyl-B12 is administered in a dose of 1-2.5 mg/day.

17. The method of claim 9, further comprising administering an effective amount of one or both of vitamin B6 and vitamin D3.

18. The method of claim 17, wherein an effective amount of both of vitamin B6 and vitamin D3 is administered.

19. The method of claim 1, wherein the one or more downstream folate compound is provided in a dose of 1 mg/day to 25 mg/day.

20. The method of claim 6, wherein the one or more compounds containing folate found downstream of folic acid in the folate cycle is 5-formyltetrahydrofolate.

21. The method of claim 13, wherein the one or more compounds containing folate found downstream of folic acid in the folate cycle is 5-formyltetrahydrofolate.

* * * * *

UNITED STATES PATENT AND TRADEMARK OFFICE
CERTIFICATE OF CORRECTION

PATENT NO.         : 10,278,987 B2                               Page 1 of 1
APPLICATION NO.    : 15/714802
DATED              : May 7, 2019
INVENTOR(S)        : Brian W. Buell It is certified that error appears in the above-identified patent and that said Letters Patent is hereby corrected as shown below:

On the Title Page

In Column 1, below "Related U.S. Application Data", Line 1, "(60)" should be -- (62) --.

In the Claims

At Column 20, Line 45, "1 mcg 25 mg/day." should be -- 1 mcg to 25 mg/day. --.

Signed and Sealed this
Nineteenth Day of November, 2019

Andrei Iancu
*Director of the United States Patent and Trademark Office*